(12) United States Patent
Reich et al.

(10) Patent No.: US 10,590,376 B2
(45) Date of Patent: Mar. 17, 2020

(54) SYSTEM FOR CONDITIONING OF ENGINEERED MICROTISSUES

(71) Applicant: THE JOHNS HOPKINS UNIVERSITY, Baltimore, MD (US)

(72) Inventors: Daniel H. Reich, Baltimore, MD (US); Fan Xu, Nanjing (CN); Ruogang Zhao, Baltimore, MD (US); Alan S. Liu, Baltimore, MD (US); Tristin Metz, Baltimore, MD (US); Yu Shi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 231 days.

(21) Appl. No.: 15/528,233

(22) PCT Filed: Nov. 20, 2015

(86) PCT No.: PCT/US2015/061800
§ 371 (c)(1),
(2) Date: May 19, 2017

(87) PCT Pub. No.: WO2016/081816
PCT Pub. Date: May 26, 2016

(65) Prior Publication Data
US 2017/0362560 A1    Dec. 21, 2017

Related U.S. Application Data

(60) Provisional application No. 62/082,374, filed on Nov. 20, 2014.

(51) Int. Cl.
*C12M 1/42* (2006.01)
*C12M 3/00* (2006.01)
(Continued)

(52) U.S. Cl.
CPC ............ *C12M 35/06* (2013.01); *C12M 21/08* (2013.01); *C12M 23/12* (2013.01); *C12M 23/20* (2013.01);
(Continued)

(58) Field of Classification Search
None
See application file for complete search history.

(56) References Cited

U.S. PATENT DOCUMENTS

| 6,218,178 B1 | 4/2001 | Banes |
| 7,553,662 B2 | 6/2009 | El Haj et al. |

(Continued)

FOREIGN PATENT DOCUMENTS

| JP | 2003-180331 A | 7/2003 |
| JP | 2008-263986 A | 11/2008 |

(Continued)

OTHER PUBLICATIONS

Cummings, C.L., et al., Properties of engineered vascular constructs made from collagen, fibrin, and collagen-fibrin mixtures. Biomaterials, 2004. 25(17): p. 3699-3706.
(Continued)

*Primary Examiner* — Blaine Lankford
(74) *Attorney, Agent, or Firm* — Johns Hopkins Technology Ventures

(57) ABSTRACT

A system and method for conditioning a tissue are provided. The system includes a substrate, a plurality of microwells formed in the substrate, and a microsphere associated with each of the plurality of microwells. The system also includes a pair of flexible pillars within each of the plurality of microwells. Each flexible pillar includes a first end bonded to a respective microwell and at least one flexible pillar has a second end bonded to the microsphere. The flexible pillars are configured to deflect when exposed to a magnetic field
(Continued)

to controllably stretch microtissue spanning the flexible pillars.

17 Claims, 6 Drawing Sheets

(51) Int. Cl.
*C12M 1/32* (2006.01)
*C12M 1/12* (2006.01)
*C12M 1/00* (2006.01)
*C12M 1/34* (2006.01)
*C12N 13/00* (2006.01)
*B01L 3/00* (2006.01)

(52) U.S. Cl.
CPC ............ *C12M 23/26* (2013.01); *C12M 25/00* (2013.01); *C12M 35/04* (2013.01); *C12M 41/00* (2013.01); *C12N 13/00* (2013.01); *B01L 3/508* (2013.01)

(56) References Cited

U.S. PATENT DOCUMENTS

| | | | |
|---|---|---|---|
| 8,375,851 | B2 | 2/2013 | Bryant et al. |
| 10,001,474 | B2* | 6/2018 | Welch ................. G01N 33/581 |
| 10,451,631 | B2* | 10/2019 | Bergo ............. G01N 33/54306 |
| 2004/0101819 | A1 | 5/2004 | Montemagno et al. |
| 2006/0282576 | A1* | 12/2006 | Hsu ....................... G06F 13/387 710/62 |
| 2009/0209035 | A1 | 8/2009 | Watanabe |
| 2011/0007955 | A1* | 1/2011 | Ho .......................... C40B 20/04 382/128 |
| 2011/0097723 | A1* | 4/2011 | Liu ........................ B82Y 15/00 435/6.1 |

FOREIGN PATENT DOCUMENTS

| | | |
|---|---|---|
| JP | 2009-254275 A | 11/2009 |
| WO | 2005007233 A2 | 1/2005 |
| WO | 2012118799 A2 | 9/2012 |
| WO | 2013119570 A1 | 8/2013 |
| WO | 2013152036 A1 | 10/2013 |

OTHER PUBLICATIONS

Legant, W.R., et al., Microfabricated tissue gauges to measure and manipulate forces from 3D microtissues. Proc Natl Acad Sci U S A, 2009. 106(25): p. 10097-102.
Boudou, T., et al., A microfabricated platform to measure and manipulate the mechanics of engineered cardiac microtissues. Tissue Eng Part A, 2012. 18(9-10): p. 910-9.
West, A.R., et al., Development and characterization of a 3D multicell microtissue culture model of airway smooth muscle. American Journal of Physiology—Lung Cellular and Molecular Physiology, 2013. 304(1): p. L4-L16.
Zhao, R., et al., Decoupling cell and matrix mechanics in engineered microtissues using magnetically actuated microcantilevers. Adv Mater, 2013. 25(12): p. 1699-705.
Lucas, K., et al. Sculpting of Nanopores in Silicon-Nitride Membranes. in APS Meeting Abstracts. 2007.
Wasserman, J., et al., Fabrication of one-dimensional programmable-height nanostructures via dynamic stencil deposition. Review of Scientific Instruments, 2008. 79(7): p. 073909-073909-4.
Andrade, P.Z., et al., Stem cell bioengineering strategies to widen the therapeutic applications of haematopoietic stem/progenitor cells from umbilical cord blood. Journal of tissue engineering and regenerative medicine, 2013.
Mannoor, M.S., et al., 3D printed bionic ears. Nano letters, 2013. 13(6): p. 2634-2639.
Seliktar, D., et al., Dynamic mechanical conditioning of collagen-gel blood vessel constructs induces remodeling in vitro. Annals of biomedical engineering, 2000.28(4): p. 351-362.
Barron, V., et al., Bioreactors for cardiovascular cell and tissue growth: a review. Annals of biomedical engineering, 2003. 31(9): p. 1017-1030.
Altman, G., et al., "Cell Differentiation by Mechanical Stress" FASEB journal, 2001.
Beca, B., et al., "A Platform for Combinatorial Mechanobiological Stimulation of Engineered Microtissues" 16th international conference on Miniaturized Systems for Chemistry and Life Sciences, 2012.
Dobson, J., "Principles and Design of a Novel Magnetic Force Mechanical Conditioning Bioreactor for Tissue Engineering, Stem Cell Conditioning, and Dynamic In Vitro Screening" IEEE Transactions on Nanobioscience, vol. 5, No. 3, Sep. 2006.
Legant, W., "Microfabricated tissue gauges to measure and manipulate forces from 3D microtissues" PNAS 2009, vol. 106, No. 25, pp. 10097-10102.
Brady, M. "The Design and Development of a High-Throughput Magneto-Mechanostimulation Device for Cartilage Tissue Engineering" Tissue Engineering: Part C, vol. 20, No. 2, 2014.
Hirt, M., et al., "Cardiac Tissue Engineering : State of the Art" Circ Res. 2014;114:354-367.
Hoerstrup S., et al., "New pulsatile bioreactor for in vitro formation of tissue engineered heart valves" Tissue Engineering, vol. 6, No. 1, 2000.
Sacks, et al., "Bioengineering Challenges for heart Valve Tissue Engineering" Annu. Rev. Biomed. Eng. 2009. 11:289-313.
Huang, A., et al., "Engineering of arteries in vitro", Cell Mol Life Sci. Jun. 2014 ; 71(11): 2103-2118.
Xu, F., et al., "A microfabricated magnetic actuation device for mechanical conditioning of arrays of 3D microtissues", Lab Chip (2015) vol. 15, No. 11, pp. 2496-2503.

* cited by examiner

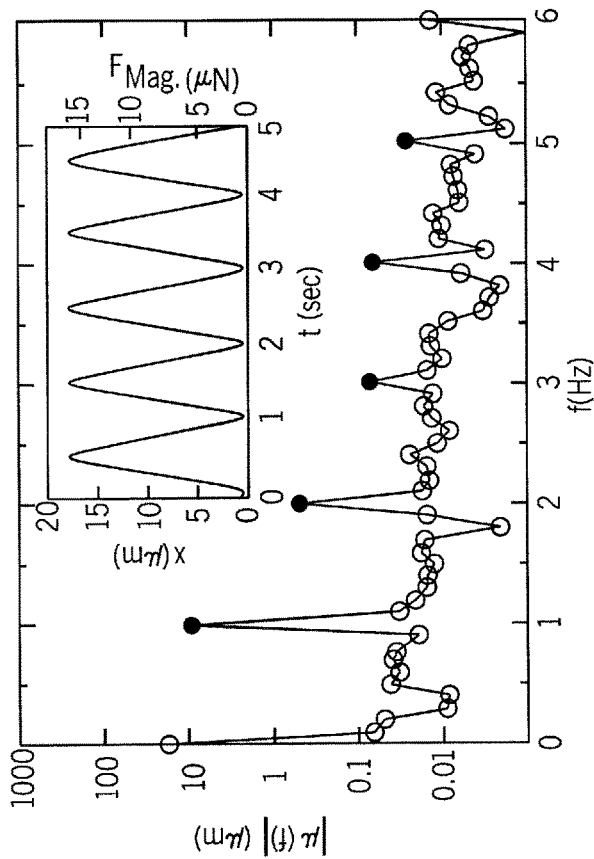
FIG. 5C
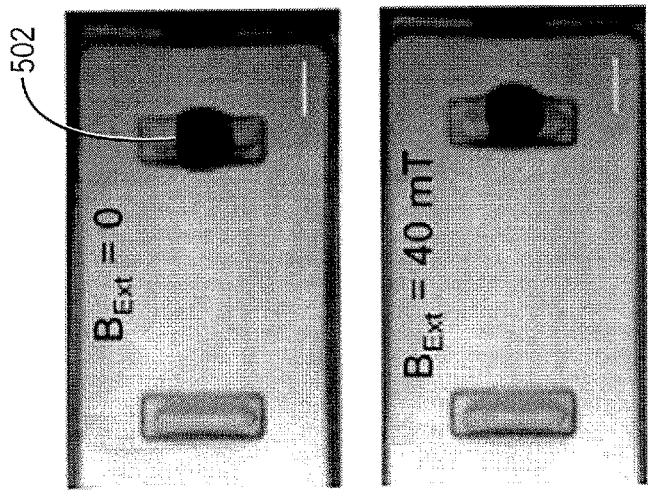
FIG. 5A
FIG. 5B

SYSTEM FOR CONDITIONING OF ENGINEERED MICROTISSUES

CROSS-REFERENCE TO RELATED APPLICATIONS

This application is a 35 U.S.C. § 371 U.S. national entry of International Application PCT/US2015/061800, having an international filing date of Nov. 20, 2015, which claims the benefit of U.S. Provisional Application No. 62/082,374, filed Nov. 20, 2014, the content of each of the aforementioned applications is herein incorporated by reference in their entirety.

STATEMENT REGARDING FEDERALLY SPONSORED RESEARCH OR DEVELOPMENT

This invention was made with government support under grant no. HL090747, awarded by the National Institutes of Health. The government has certain rights in the invention.

BACKGROUND

The present disclosure relates generally to mechanical conditioning of engineered tissues and, more particularly, systems and methods for conditioning or controlling processing of microtissues.

Engineered biological tissues provide the potential for options beyond the traditional treatments, for example, when testing drugs in development, and when performing tissue and organ repair. In addition, these tissues allow for the study of the organization and mechanical and biological function of model multicellular constructs. Static and dynamic mechanical conditioning during the engineering process have been found to enhance tissue structure, mechanical strength, and overall functionality. Mechanical conditioning of these engineered tissues traditionally requires the use of centimeter scale tissue samples and potentially complex bioreactor systems. The large scale of the tissues sets a limit to the imaging which can be performed on the tissue and the ability for pharmacological treatments to diffuse throughout.

Current cutting edge methods of tissue engineering range from bioreactors to 3D printing. The majority of these methods, however, use relatively large amounts of reagents and do not condition the tissue as it matures. The expense of certain reagents and the rarity of certain cell lines necessitate a method for high-throughput tissue engineering that uses few materials. Furthermore, conditioning is an important step that contributes to the tissues' ultimate mechanical integrity.

A range of microengineered devices fabricated from soft materials, such as poly(dimethylsiloxane) (PDMS), have been developed that can measure the force generation (contractility) of model tissues of the millimeter and sub-millimeter scales during the process of tissue conditioning. In these devices, cells and extracellular matrix self-assemble under the contractile action of the cells into tissue constructs suspended between a pair of flexible vertical cantilevers, whose deflection reports the net contractile force generated by the cells in the tissue. These microtissue strain gauges have enabled the study of contractility in a range of model tissues, involving fibroblasts, airway smooth muscle cells, and cardiomyocytes.

The capability of such force measuring devices can be greatly expanded by enabling actuation of the microtissues, as this can allow further exploration of the properties of such tissue constructs. In addition, actuation allows for analysis of both acute and long-term response to mechanical conditioning of the specific tissues. It would be desirable to have a system and method that allows for further actuation of tissue constructs during a conditioning and measuring process.

SUMMARY

The present disclosure overcomes the aforementioned drawbacks by providing a system and method for non-invasive actuation of tissues to mechanically condition such tissue. For example, a system and method is provided for mechanical actuation of an array of microtissues. When paired with a magnetic microtissue tester (MMT), the contractility of the tissue can be accurately monitored during the conditioning process.

In accordance with one aspect of the disclosure, a system and method for conditioning a tissue are provided. The system includes a substrate, a plurality of microwells formed in the substrate, and a microsphere associated with each of the plurality of microwells. The system also includes a pair of flexible pillars within each of the plurality of microwells. Each flexible pillar includes a first end bonded to a respective microwell and at least one flexible pillar has a second end bonded to the microsphere. The flexible pillars are configured to deflect when exposed to a magnetic field to controllably stretch microtissue spanning the flexible pillars.

In accordance with another aspect of the disclosure, a method of conditioning tissue is provided that includes introducing sample cells into one or more microwells to extend as microtissue across a plurality of pillars. The method also includes magnetizing the nickel microsphere and pillars using an externally-applied magnetic field to displace the pillars and apply a force to the microtissue and monitoring mechanical properties of the microtissue while repeatedly adjusting the magnetizing of the nickel microsphere and pillars to perform a tissue conditioning process.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5A is an image of an MMT without an external magnetic field applied

FIG. 5B is an image of an MMT with an external magnetic field applied

FIG. 5C is a graph of the motion of a pillar in response to the external magnetic field in accordance with the present disclosure.

DETAILED DESCRIPTION

An approach has been demonstrated that enables mechanical stimulation of microtissues via magnetic actuation of magnetic microspheres bonded to the cantilevers of arrays of microtissue strain gauges. This approach allows for the measurement of the mechanical stiffness of the tissue constructs, and analysis of the relative contribution of cells and matrix to relevant mechanical properties. Additionally, investigation of the role of boundary conditions and mechanical constraints on tissue formation can be performed. While previous methods demonstrate the potential of magnetically driven microtissue constructs, actuation has been performed using an electromagnetic tweezer device. This approach requires invasive probing as the pole tip of the electromagnet must be inserted into the culture media.

The present disclosure provides a device for actuating and conditioning microtissues. When paired with a magnetic microtissue tester (MMT), the device acts as a less resource intensive means of tissue engineering and as a method to influence and test tissue mechanical properties.

Figure 1A:
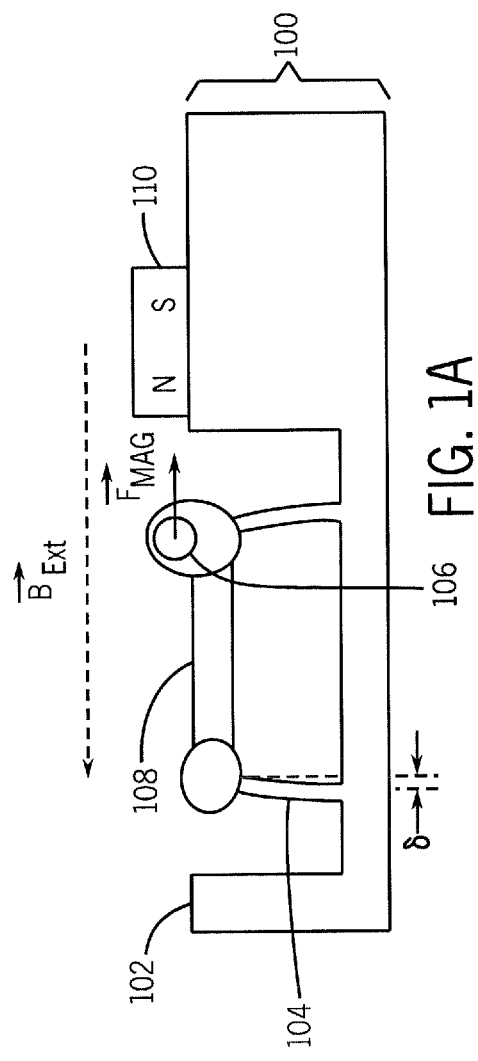
FIG. 1A is a schematic illustration of a microwell containing the actuation device and a magnetic microtissue tester (MMT) in accordance with the present disclosure.

The present approach allows for simultaneous magnetically-driven mechanical actuation of an array of microtissue strain gauges (µTUGs) 100. FIG. 1(a) illustrates one microwell 102 which may be used in a broader system that may incorporate more than one microwell 102, each containing flexible pillars 104 that may be fabricated in a PDMS substrate with, for example, a magnetic Nickel microsphere 106 bonded to one of the pillars 104. Though a pair of pillars 104 is illustrated, this is a non-limiting example. For example, other numbers of pillars 104 beyond pairs, for example, 4 or 8 pillars, or odd numbers of pillars may be included. A mixture of cells and extracellular matrix (ECM) is introduced into the wells 102, and as the cells contract the mixture, they form an aligned microtissue 108 spanning the pillars 104, which bend due to the collective contractile force of the microtissue 108, providing a read-out of the force. A small (~1 mm) Nickel bar 110 is microfabricated on a silicon wafer, and is placed near the magnetic pillar 104. When the sphere 106 and bar 110 are magnetized by an externally applied magnetic field, the sphere is attracted to the bar with a magnetic force, which controllably stretches the microtissue 108.

In one aspect of the disclosure, a PDMS MMT device can be created in conjunction with an actuation device. The PDMS MMT device facilitates the formation of the microtissues, which will be magnetically activated by the actuation device. In one example embodiment of the PDMS MMT device, PDMS molds are used for replica molding. The PDMS molds include pairs of flexible pillars 104 with, as a non-limiting example, separation of 500 µm in wells 102 with, as a non-limiting example, dimensions 800 µm×400 µm×170 µm deep. In addition, as a non-limiting example, the PDMS may have an elastic modulus of 1.6 MPa. The pillars 104 may have, as a non-limiting example, a length of 115 µm and cross section of 140 µm×35 µm in their flexible sections, giving them an effective spring constant of k=0.9 µN/µm for small deflections. Nickel spheres 106, as a non-limiting example, may have ~100 µm diameters and be bonded with PDMS to the top of one pillar in each MMT.

In one example, the microtissues 108 are formed by introducing suspensions of NIH 3T3 fibroblasts and 2.5 mg/ml unpolymerized rat tail type-I collagen (BD Biosciences) into the wells 102. The cells are cultured on the MMT devices for two days prior to measurements in high glucose Dulbecco's Modified Eagle's Medium, supplemented with 10% bovine serum, 100 units/ml penicillin, and 100 µg/ml streptomycin (all from Invitrogen).

Figure 1B:
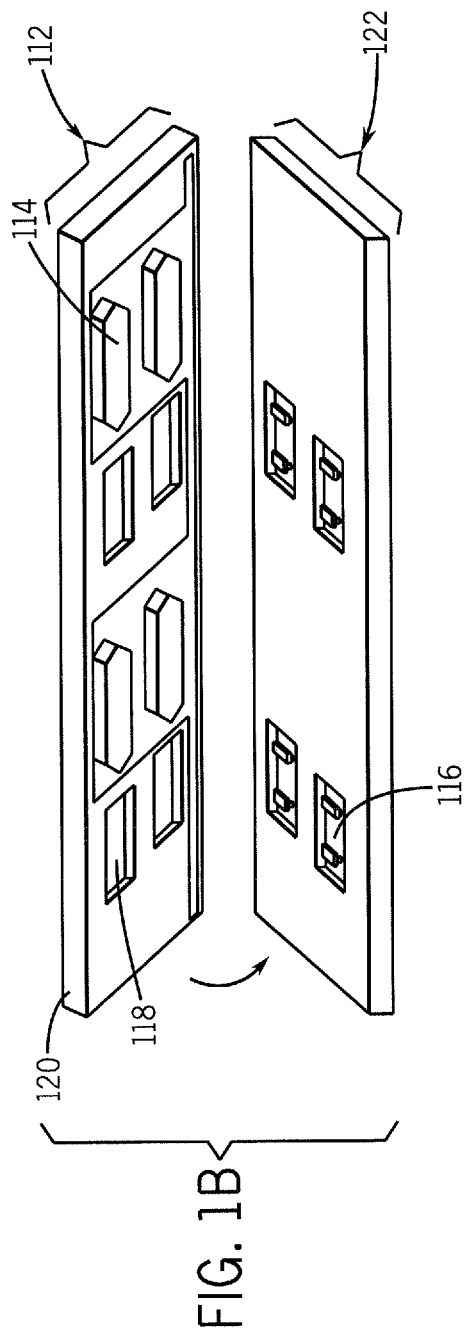
FIG. 1B is schematic illustration of an array of microwells containing magnetic microtissue testers (MMT) to create a magnetic microtissue actuation system to condition and test an array of tissues in accordance with the present disclosure.

FIG. 1(b) illustrates the present approach in an array format, with a schematic of a magnetic microtissue actuation system, with multiple nickel bars 114 that align with the individual µTUGs 116, microtissues and the inclusion of an array of holes 118 etched through the Si wafer 120 to enable optical access and good exchange of culture media for the microtissues. The actuation device 112 is made up of a through-etched silicon nitride-coated wafer 120 with patterned gold fingers. Nickel islands 114 are created on top of the gold circuitry via electrodeposition in order to transduce an externally applied uniform magnetic field into a local inhomogeneous field near each MMT 122. That is, the nickel bars 114 may be patterned on a silicon wafer 120. Alternatively, the nickel bars 114 may be mounted directly on the PDMS MMT device, as generally illustrated in FIG. 1(a).

The construction of the actuation device can be broken down into three segments: gold circuitry definition, nickel electro-deposition, and wafer through-etching. The component steps in the latter two processes can be interleaved to ensure survivability of the features on the substrate.

The actuation device is constructed using standard photolithography and electrodeposition techniques, and represents a simple to design, easy to create device for tissue mechanical conditioning and testing. The techniques used for fabrication allow for highly uniform actuation device production.

A schematic illustration of a fabrication process for the actuation device can be seen in FIG. 2. This process includes the steps of fabricating the gold fingers on the silicon nitride-coated wafers, spinning a photoresist layer over the gold fingers, defining the desired shape of the nickel bars in the resist layer, defining a mask for the wafer through-etching, electrodepositing the nickel bars in the previously defined mask, and etching holes in the wafer.

Turning to FIG. 2, one example fabrication process is shown. Patterned metal (Cr(7 nm)/Au (45 nm)) finger-shaped arrays 202 that are 1,600 μm wide were fabricated on double-side polished silicon-nitride coated wafers 204 using standard photolithography, thermal evaporation, and lift-off processing techniques which can be seen in FIG. 2(a). The position and size of the metal fingers were designed to align along the short edge of each individual microwell, and fit to the empty space between two adjacent microwells. A 120 μm thick layer of SU-8 photoresist 206 was then spun between the gold fingers, and patterns corresponding to the shape of the nickel bars were defined in the SU-8 layer on the gold fingers as seen in FIG. 2(b). To ensure clean gold surfaces for the subsequent nickel electrodeposition, the top side of the substrate was reactive-ion etched (RIE) in $O_2$ for 5 minutes to remove any remaining SU-8 on the exposed gold regions. Next, to define a mask for the wafer through-etching, an array of rectangular holes 208, each of dimension 1,200 μm by 840 μm, was patterned into the silicon-nitride coating using S1813 210. The holes 208 were patterned on the side of the wafer opposite the gold fingers via backside alignment, using standard photolithography and reactive ion etching in $CF_4$ and $O_2$, as shown in FIG. 2(c).

Figure 2A:
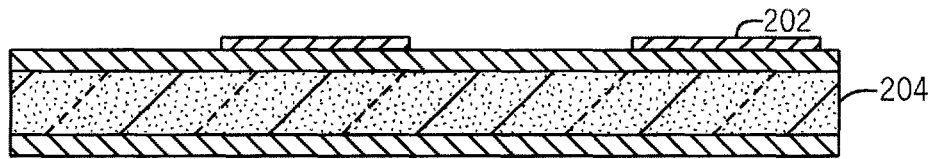
FIG. 2A is schematic illustration of an actuation device in accordance with the present disclosure in one state of a fabrication process in accordance with the present disclosure.
Figure 2B:
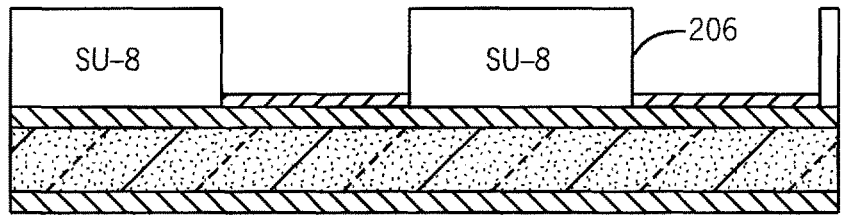
FIG. 2B is schematic illustration of an actuation device in accordance with the present disclosure in another state of a fabrication process in accordance with the present disclosure.
Figure 2C:
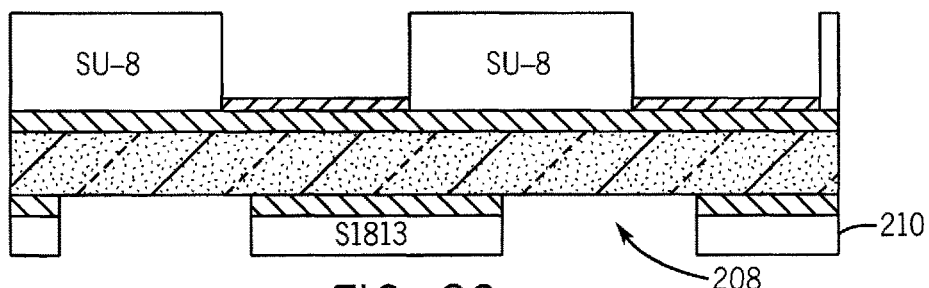
FIG. 2C is schematic illustration of an actuation device in accordance with the present disclosure in yet another state of a fabrication process in accordance with the present disclosure.
Figure 2D:
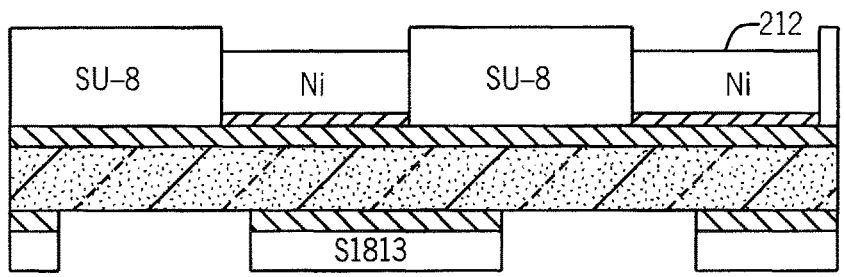
FIG. 2D is schematic illustration of an actuation device in accordance with the present disclosure in still another state of a fabrication process in accordance with the present disclosure.

As can be seen in FIG. 2(d), the nickel bars 212 were then electrodeposited onto the previously defined patterns to thicknesses of 50-100 μm, as desired, using the gold finger array as a working electrode. The nickel deposition solution consisted of 80.5 g nickel (II) sulfamate, 6.25 g nickel chloride, 10 g boric acid, and 0.05 g sodium dodecyl sulfate (SDS), in 250 mL water. For deposition, a potentiostat (Model 263A, Princeton Applied Research) was used in galvanostatic mode and was set to −1 V relative to a platinum reference electrode.

Figure 2E:
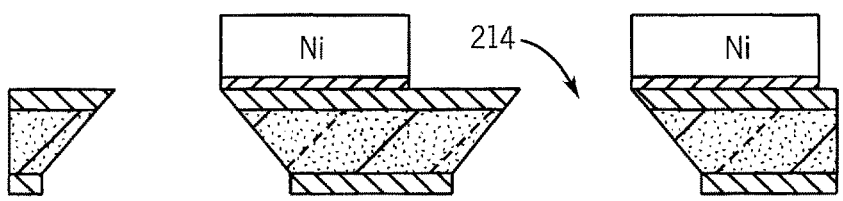
FIG. 2E is schematic illustration of an actuation device in accordance with the present disclosure in still another state of a fabrication process in accordance with the present disclosure.

Finally, as seen in FIG. 2(e), the holes 214 in the wafer were produced by etching in a 30% KOG solution at 150° C. for approximately 6 hours to obtain holes on the side of the wafers with the nickel bars that match the dimensions of the wells on the MMTs. The KOH bath had the added effect of removing any remaining photoresist adhered to the wafer.

To characterize the properties of the actuation device, several measurement devices were used. The lateral dimensions of the device features were verified using optical microscopy. The thickness and uniformity of the nickel bars were measured by optical profilometry (VK-VX100, Keyence). Finally, the magnetic properties of the nickel bars were determined by removing individual nickel bars from the silicon wafers, and measuring the bars in a vibrating sample magnetometer (VSM) (DMS Model 10; ADE Technologies, Westwood, Mass.).

Figure 3B:
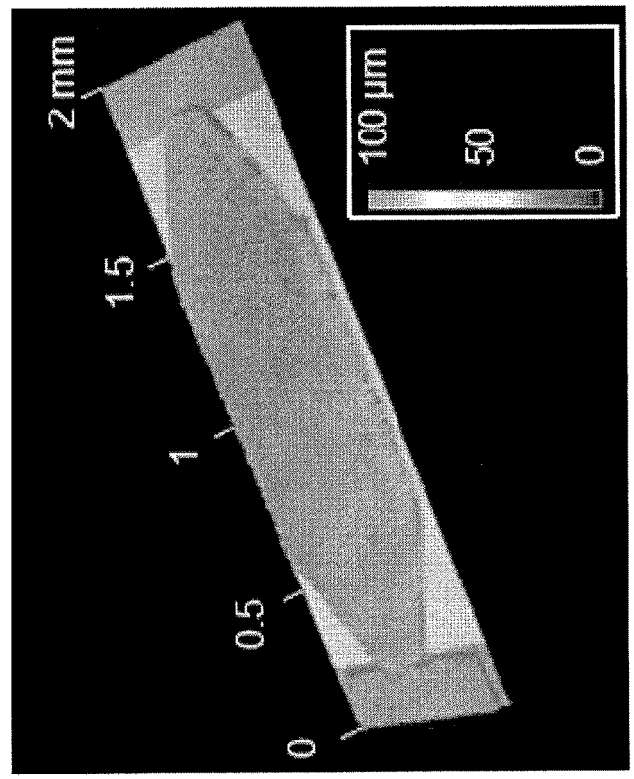
FIG. 3B is another illustration of the geometric characterization of the actuation device in accordance with the present disclosure.
Figure 3A:
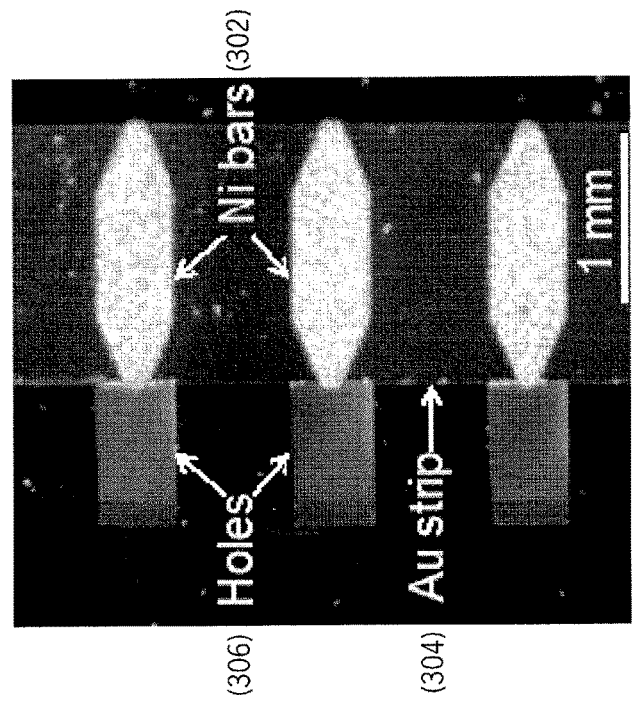
FIG. 3A is a schematic illustration of the geometric characterization of the actuation device in accordance with the present disclosure.

To test the fabrication and measurement procedures for the actuation devices, arrays containing up to 20 electrode-posited nickel bars and corresponding through-holes on segments of silicon-nitride coated silicon wafers may be produced. FIG. 3(a) illustrates a portion of one such array, showing three nickel bars 302, their underlying Au strip 304, and corresponding through-holes 306. The nickel bars are fabricated with pointed ends to concentrate magnetic flux and create larger field gradients in the neighborhood of the magnetic pillars. The bars shown have length 1,600 μm, width 450 μm, and tip width 90 μm. To achieve alignment with the MMT arrays, in this configuration, the nickel bars are laid out on a rectangular grid with center-to-center spacing of 3,200 μm along the bars' long axis and 1,200 μm along the short axis.

The dimensions of the nickel bars may be characterized via optical profilometry. FIG. 3(b) shows the height profile of a nickel bar. The lateral dimensions of the electrodeposited bars vary by <0.6% along the long axis, and <2% along the short axis in this configuration. Individual bars are flat, with height variations of less than 2%. A variation of ~10% is found in the bars' thicknesses t=60±7 μm (N=27), likely from variations in the deposition current across the arrays.

The PDMS-MMT device together with actuation device provide a system for mechanically activating the microtissue, and calculating mechanical properties such as stress, strain, and stiffness. By mounting the actuation device on the PDMS-MMT device, a system is created that can allow for electromagnetic activation of the actuation device and stimulation of the microtissues that have been formed on the PDMS-MMT device.

In one example, measurements and probing of microtissue occur when the actuation device is mounted and aligned under a microscope on the MMT device, and the arrays are actuated with a microscope-mounted dual-coil programmable electromagnet. The electromagnet used is capable of producing magnetic fields of up to 50 mT with a uniformity of 3% over the largest arrays studied.

Images of individual MMTs and microtissues may be obtained using phase contrast microscopy with a 10× objective on a Nikon TE-2000E inverted microscope. For mechanical measurements of individual microtissues a quasi-static stretching protocol is used, during which images were recorded with a CoolSnap HQ (Photometrics) camera. To characterize sinusoidal actuation, movies are recorded at 100 frames/sec using a Prosilica GX (Allied Vision Technologies) camera. The pillar deflections are determined from the images using Image) (NIH) for the quasi-static measurements and via custom tracking software written in IgorPro (WaveMetrics) for the dynamic actuation studies.

Figure 4A:
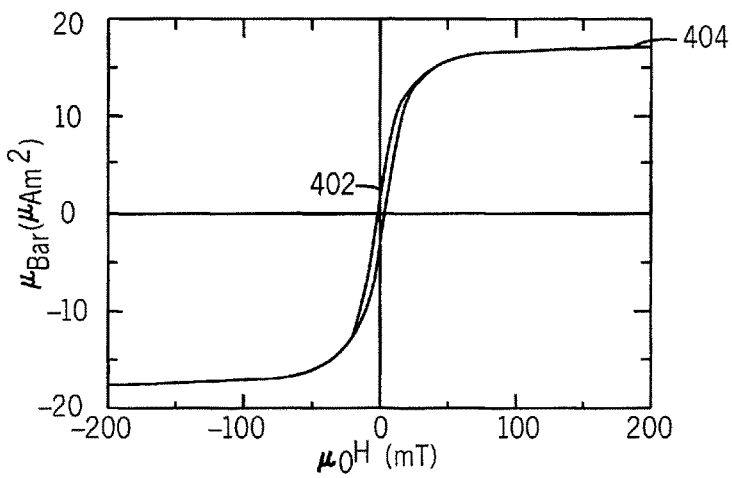
FIG. 4A is a graph illustrating characteristics of an example for magnetic characterization of a system in accordance with the present disclosure.
Figure 4B:
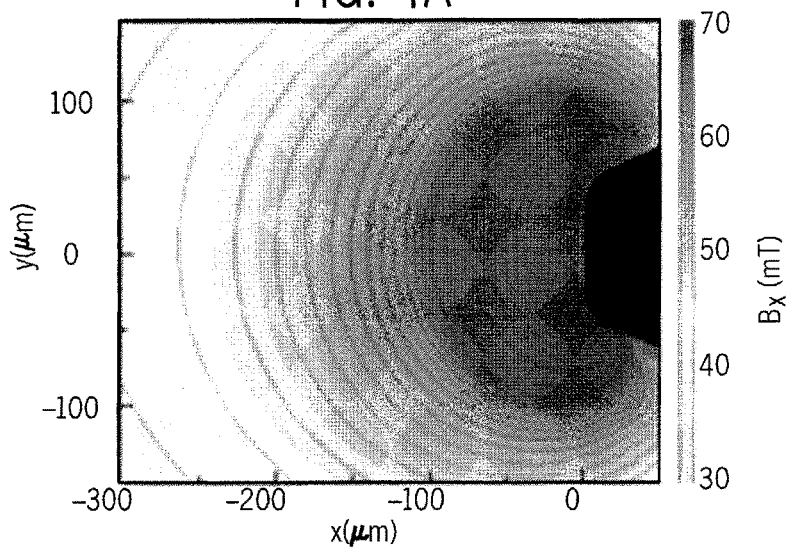
FIG. 4B is another graph illustrating characteristics of an example for magnetic characterization of a system in accordance with the present disclosure.
Figure 4C:
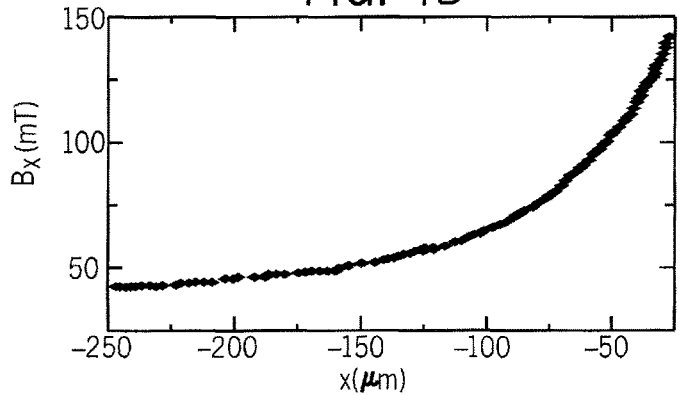
FIG. 4C is yet another graph illustrating characteristics of an example for magnetic characterization of a system in accordance with the present disclosure.

The stress, strain, and elastic modulus of each microtissue is determined from the quasi-static stretching data. Briefly, the force on each microtissue is found by tracking the deflection of the non-magnetic MMT pillar and calculating a force based on its spring constant. The stress in the central region of each microtissue is then obtained from the measured dimensions of the microtissue. The strain is measured locally in the microtissues' centers from sequential phase contrast images, using a texture correlation analysis algorithm. The elastic modulus is determined from the slope of the resulting stress-strain curves FIG. 4(a) shows the magnetic moment $\mu_{Bar}$ vs. applied magnetic field $\mu_0 H$ for a representative nickel bar removed from the array and measured using a vibrating sample magnetometer (VSM). As shown in FIG. 4(a), the magnetic hysteresis of the bars is small, with a remnant moment 402 approximately 10% of the bars' saturation moment $\mu_{Sat}$ 404. It can be noted that the measured value of $\mu_{Sat}$=1.72 μAm² agrees with the value expected for the design dimensions and the room temperature saturation magnetization of nickel. FIGS. 5(a) and 5(b) show the deflection of a magnetic pillar 502 due to the force produced by the nickel bar on the actuation device in an applied external magnetic field $B_{Ext}$=40 mT. To assess the variability of the force generation, a set of MMTs on an array is measured, and deflections of 17.4±2.5 μm ($F_{Mag}$=15.7±2.3 μN) are found in a field $B_{Ext}=34$ mT (N=9). FIGS. 4(b) and 4(c) show a finite-element modeling computation in the vicinity of one end of a nickel bar of the component $B_x$ of the magnetic field parallel to a bar's long axis in an external field of 34 mT, using the COMSOL Multiphysics package. Hysteresis effects are not included. From this, the force on a nickel bead on an adjacent MMT pillar may be estimated as $F_{Mag}=\nabla(\mu_{Sph}(B)\cdot B)$, where $\mu_{Sph}$ is the field-dependent magnetic moment of the nickel sphere in the total field $B=B_{Ext}+B_{Bar}$. At a bar-sphere spacing of 150 µm, the calculation shown in FIGS. 4(b) and 4(c) yields $B=51.1$ mT and $dB_x/d_x=180$ T/m. At this field, the nickel spheres have $\mu_{Sph}=0.075$ µA m², which yields $F_{Mag}\sim 14$ µN, in reasonably good agreement with our measured value.

In another embodiment of the disclosure, the actuation device applies a quasi-static load on the microtissue. By applying a magnetic field to the actuation device, the magnetic pillars are pulled toward the nickel bars.

To determine the suitability of the device for AC stimulation, the response of the magnetic pillars to sinusoidal external fields is measured. An example of a magnetic pillar's motion in response to a 0.5 Hz AC magnetic field of amplitude 20 mT is shown in the inset to FIG. 5(c). Since $F_{Mag}=\nabla(\mu_{Sph}(B)\cdot B)$, the force and displacement are approximately quadratic in $B_{EXt}$. This leads to a frequency doubling for a sinusoidal driving field, and so the motion of the pillar is at 1 Hz. This motion is nearly sinusoidal with minimal distortion. Indeed, for the data shown in the inset of FIG. 5(c), the Fourier amplitude of the largest harmonic present (at f=2 Hz) is only 5% of the 1 Hz fundamental (FIG. 5(c), main panel), and thus despite the modest hysteresis of the bar (FIG. 4(a)) and the nickel sphere, it can be seen that this system can apply clean periodic signals at physiologically relevant frequencies.

In another embodiment of the disclosure, the system allows for dynamic loading of the tissue. Cyclic loading of the actuation device causes motion of the pillars, inducing an active load in the tissues by the pillar and a tension force on the pillars by the microtissue.

Figure 6B:
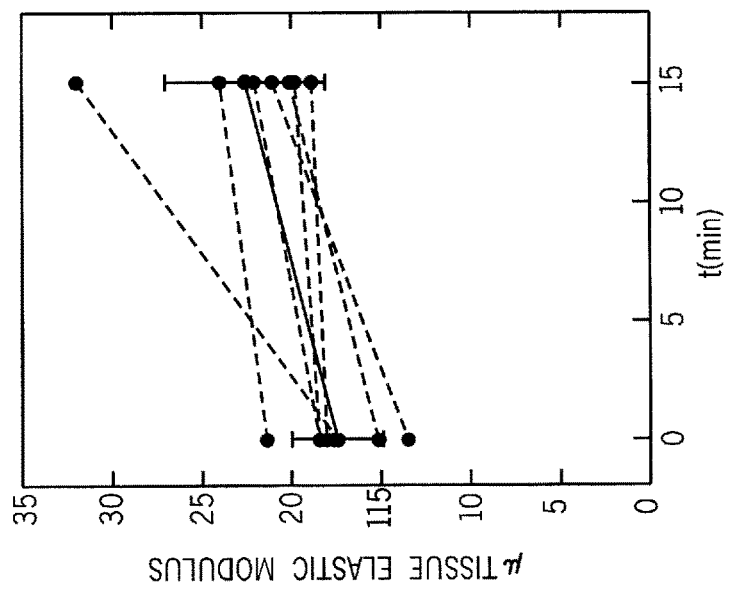
FIG. 6B is a graph of stiffness changes of microtissue characterized by elastic modulus during dynamic loading.
Figure 6A:
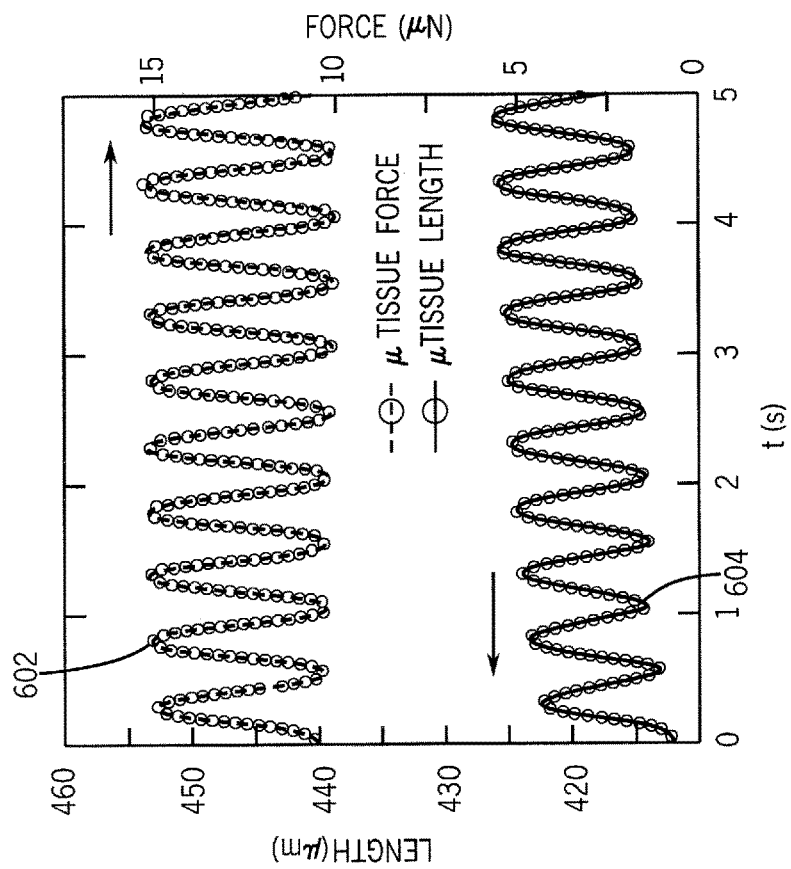
FIG. 6A is a graph of stiffness changes of microtissue characterized by force and length during dynamic loading.

The dynamic loading capacity of the actuation device is evaluated by applying a sinusoidal magnetic external field of amplitude 20 mT at 1 Hz to the actuation devices on MMTs. To verify that the microtissues undergo periodic actuation in response to this stimulation, the microtissues are observed for brief intervals (~15 sec) while recording their motion at 100 frames/sec. FIG. 6(a) shows the left pillar displacement (microtissue force) 602 and overall length (difference in pillar positions) 604 vs. time for a microtissue following initiation of actuation. Both the force and length are predominantly sinusoidal with second harmonic content <6% of the 2 Hz fundamental, similar to that observed for AC actuation of magnetic pillars without microtissue as shown in FIG. 5.

To test the actuation device's potential for longer-term actuation, the elastic modulus of a set of microtissues is first measured by quasi-static loading with the actuation device as described in earlier. Cyclic loading at 2 Hz (1 Hz external field) is then applied simultaneously to the tissues for 15 min, and the stiffness is re-measured. While there is some variability in the degree of stiffness change, all microtissues measured exhibit an increase in modulus, with an average increase of 31%, which can be seen in FIG. 6(b).

This stiffness change reflects one of a reorganization of the collagen matrix, as it has been shown that cells play a minor role in fibroblast microtissue stiffness, or an actuation of internal force generation machinery. Thus, the ability of the device to influence tissue stiffness through AC stimulation has been demonstrated. In a bioengineering context, the device and associated apparatus are small enough to fit into a standard incubator. Using the device to mechanically condition tissues with AC stimulation as they are maturing is a simple extension of current protocols. Due to the versatility and efficiency of the present device, a possible application is for pharmacological mechanical testing that requires using expensive drugs and rare cell lines.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for conditioning a tissue comprising:
   a substrate;
   a plurality of microwells formed in the substrate;
   a microsphere associated with each of the plurality of microwells;
   a pair of flexible pillars within each of the plurality of microwells, each flexible pillar of the pair of the flexible pillars including a first end bonded to a respective microwell and at least one flexible pillar having a second end bonded to the microsphere; and
   wherein the pair of flexible pillars are configured to deflect when exposed to a magnetic field to controllably stretch microtissue spanning the pair of flexible pillars.

2. The system of claim 1 wherein the flexible pillars are configured to bend due to a collective contractile force of the microtissue and wherein a degree of bend of the flexible pillars provides a read-out of a force associated with the microtissue.

3. The system of claim 1 further comprising a magnetic microtissue tester (MMT) configured to assess a contractility of the microtissue during repeated deflection of the flexible pillars to perform a tissue conditioning process.

4. The system of claim 1 further comprising a plurality of silicon-nitride coated wafers bonded to the substrate, each silicon-nitride coated wafer of the plurality of silicon-nitride coated wafers being arranged between the pairs of flexible pillars.

5. The system of claim 4 further comprising a plurality of magnetic bars microfabricated on the silicon-nitride coated wafers.

6. The system of claim 4 further comprising an array of holes extending through the silicon-nitride coated wafers.

7. The system of claim 6 wherein the array of holes include etched holes.

8. The system of claim 4 further comprising gold circuitry disposed on the silicon-nitride coated wafers.

9. The system of claim 8 further comprising nickel islands electro-deposited on the gold circuitry.

10. The system of claim 1 further comprising a plurality of magnetic bars and wherein the deflection of the flexible pillars is due to a magnetic attraction between the microspheres and magnetic bars in the presence of the magnetic field.

11. The system of claim 1 wherein the substrate includes a poly(dimethylsiloxane) PDMS substrate.

12. The system of claim 1 further comprising a magnet configured to apply the magnetic field.

13. The system of claim 12 wherein the magnet is a dual-coil programmable electromagnet.

14. The system of claim 12 wherein the magnet is configured to apply a dynamic magnetic field.

15. The system of claim 12 wherein the magnet is configured to apply a quasi-static magnetic field.

16. The system of claim 1 wherein the microspheres are nickel.

17. The system of claim 1 further comprising:
a plurality of silicon-nitride coated wafers bonded to the substrate, each arranged between the pairs of flexible pillars; and
a plurality of magnetic bars including nickel and microfabricated on the silicon-nitride coated wafers.

* * * * *